US00PP31076P3

(12) United States Plant Patent
Warren

(10) Patent No.: US PP31,076 P3
(45) Date of Patent: Nov. 19, 2019

(54) CRABAPPLE TREE NAMED 'JFS KW214MX'

(50) Latin Name: *Malus*
Varietal Denomination: JFS KW214MX

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 15/932,166

(22) Filed: Feb. 14, 2018

(65) Prior Publication Data

US 2019/0254206 P1 Aug. 15, 2019

(51) Int. Cl.
*A01H 5/08* (2018.01)
*A01H 6/74* (2018.01)

(52) U.S. Cl.
USPC ..... Plt./173
CPC ..... *A01H 6/7418* (2018.05)

(58) Field of Classification Search
USPC ..... Plt./173
CPC ..... A01H 6/74; A01H 5/08
See application file for complete search history.

*Primary Examiner* — Keith O. Robinson
(74) *Attorney, Agent, or Firm* — Klarquist Sparkman, LLP

(57) ABSTRACT

A variety of crabapple which combines a combination of a narrow, upright columnar growth habit, short internodes resulting in compact growth, attractive white flowers, slightly glossy dark green foliage, persistent red fruit, and a strong resistance to the diseases fireblight and apple scab.

10 Drawing Sheets

Latin name of the genus and species of the plant claimed: *Malus*.

Variety denomination: 'JFS KW214MX'.

BACKGROUND OF THE INVENTION

In the fall of 1999, I collected open pollinated fruit from 21 experimental crabapple seedling trees, none of which were patented or introduced, and all of which have been subsequently destroyed. I extracted seed from these fruits and sowed the seed into seedbeds in a nursery in Boring, Oreg. I grew the resulting seedlings during the summer of 2000, then dug and transplanted them into a bed on wider spacing in the spring of 2001. During the late spring and summer of 2001, I inoculated these seedlings with apple scab fungus and I marked all seedlings showing infection for destruction. From this transplant bed, I kept and transplanted 1015 seedling trees that showed a degree of resistance to apple scab. During the summer of 2003, I selected a compact, upright, green-leafed tree that demonstrated moderately strong resistance to apple scab and I named it 'KW-78MX' (unpatented). I transplanted the 'KW-78MX' tree into an evaluation block in March of 2004. I evaluated 'KW-78MX' over the next two years and decided that, while its upright form was important for future breeding and selection, it was not good enough for introduction because its white flowers were slightly small compared to existing commercial cultivars and its fruits were too large for landscape use. All of these trees were grown in the same Boring, Oreg. nursery.

In the fall of 2006, I collected open pollinated fruit from the 'KW-78MX' tree. From these, I extracted seed and sowed the seed in beds. I obtained 273 seedlings generated from the seed from the 'KW-78MX' tree. I transplanted these seedlings on wider spacing in a nursery bed in the spring of 2008, inoculated these seedlings with apple scab and evaluated them for disease resistance. From this bed, I kept 33 open pollinated seedling trees from the seed from the 'KW-78MX' tree that showed resistance to apple scab and healthy foliage and I destroyed the others. These 33 seedling trees were planted in April of 2009 on wider spacing in a nursery row for further evaluation. During the summer of 2011, I selected five trees from these 33 open pollinated seedlings with unusually columnar growth habits. In the spring of 2012, I transplanted these five trees to a long term evaluation block and destroyed the other 28.

Of these five trees, one, which I named 'JFS KW214MX' possessed an outstanding and unique combination of a strongly columnar habit, slightly glossy dark green foliage, attractive white flowers, relatively small, persistent red fruit, strong resistance to apple scab and fireblight diseases. The 'JFS KW214MX' tree is the subject of this description. Of the other four trees, three have been rejected in the selection process for disease susceptibility and inferior foliage quality, but have been retained in the row for possible future breeding. One additional tree of these five columnar selections has been named 'JFS KW213MX' and is the subject of U.S. Plant patent application Ser. No. 15/932,167. All of the above trees were grown and selected in the same Boring, Oreg. nursery.

In the summers of 2011, 2013, and 2014, I collected propagating wood from the original 'JFS KW214MX' tree and directed asexual propagation by budding onto *Malus* rootstock in small experimental plots in a Canby, Oreg. nursery. This propagation resulted in 9, 8, and 10 trees, respectively. I evaluated these propagated trees in subsequent years and determined that these asexually propagated trees show that the characteristics of my new tree are firmly fixed and identical to my original tree in every manner that has been observed. Of these propagated trees, all were destroyed after evaluation except for one that was budded in 2011 which was planted in the same Boring, Oreg. evaluation block as the original tree.

BRIEF SUMMARY OF THE INVENTION

This new cultivar possesses a unique combination of characteristics that have proven firmly fixed in asexually propagated progeny and that comprise a combination of a narrow, upright columnar growth habit, short internodes resulting in compact growth, attractive white flowers, slightly glossy green foliage, relatively small, persistent red fruit, and strong resistance to the diseases fireblight and apple scab.

BRIEF DESCRIPTION OF THE DRAWING

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
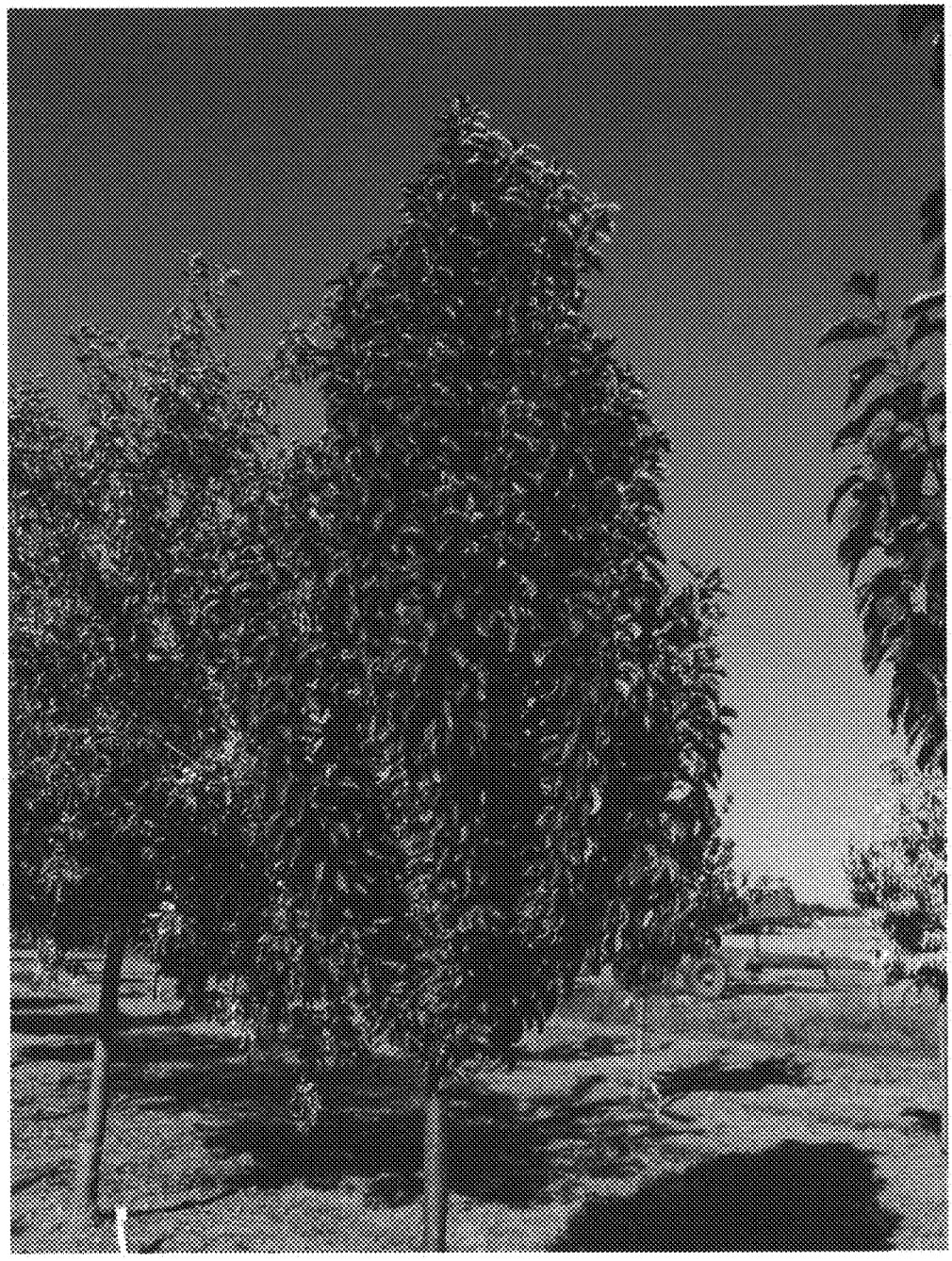
FIG. 1: Shows the original tree at 7 years old with summer foliage illustrating its narrow upright columnar shape
Figure 2:
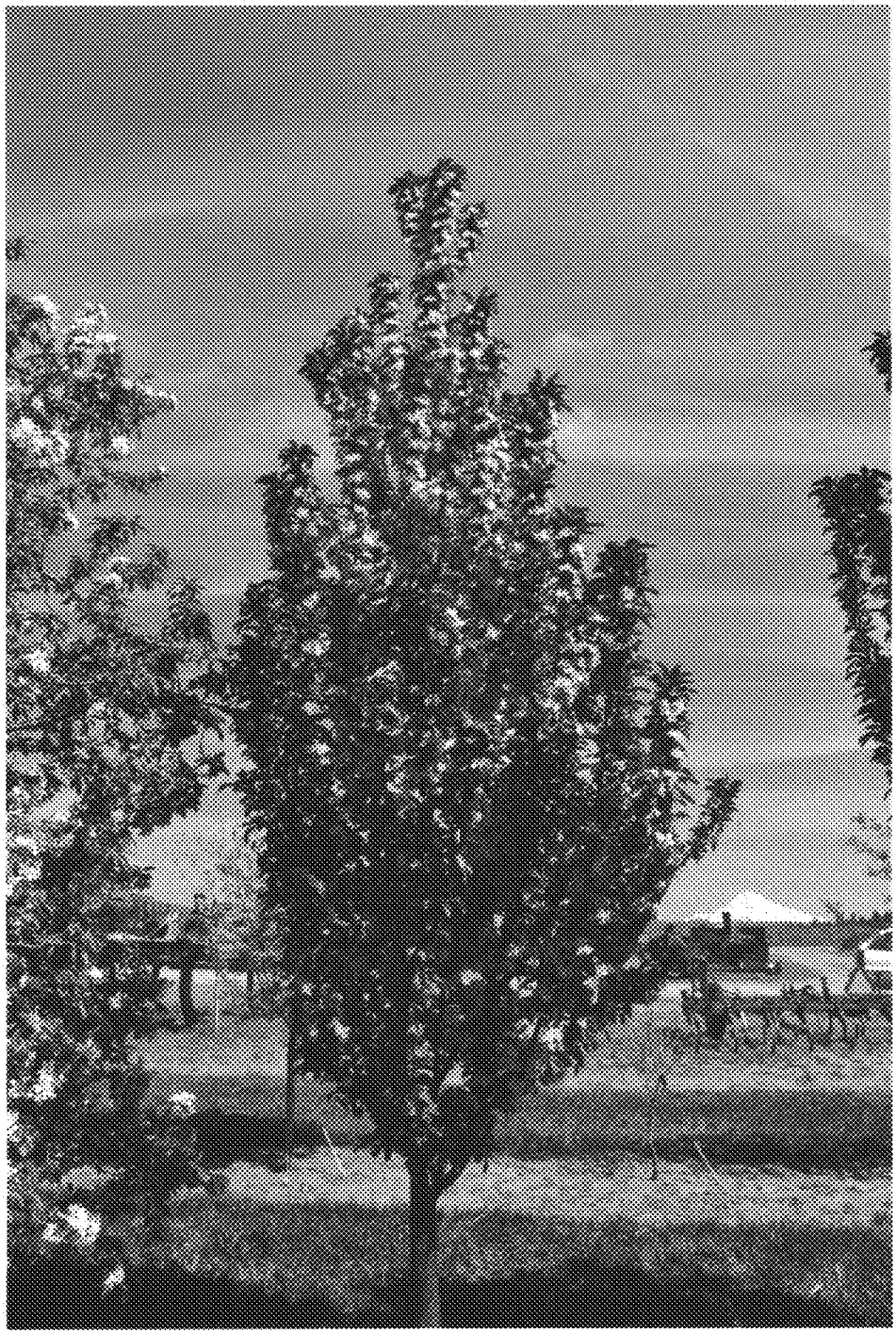
FIG. 2: Shows the original tree in flower at 10 years of age.
Figure 3:
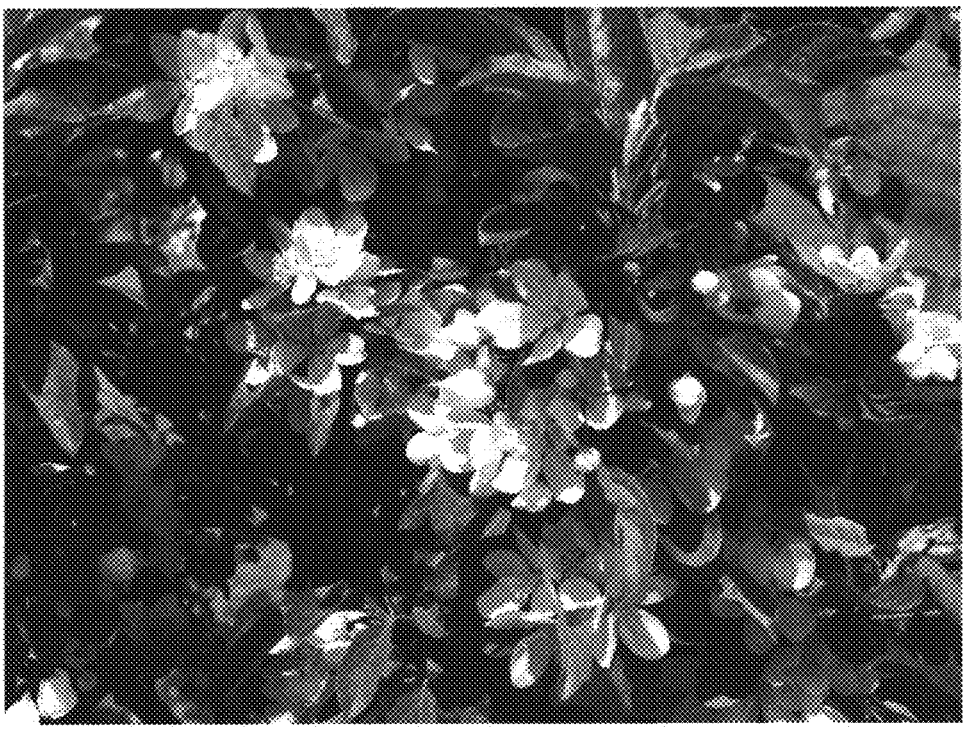
FIG. 3: Shows a close-up of the flowers on the original tree.
Figure 4:
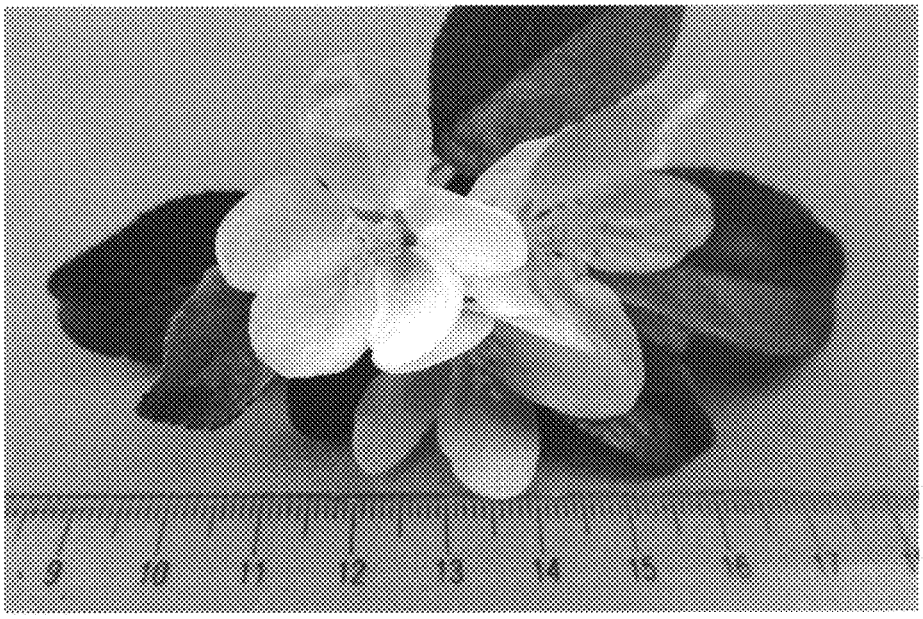
FIG. 4: Shows a close up of a few flowers on a display board with a scale.
Figure 5:
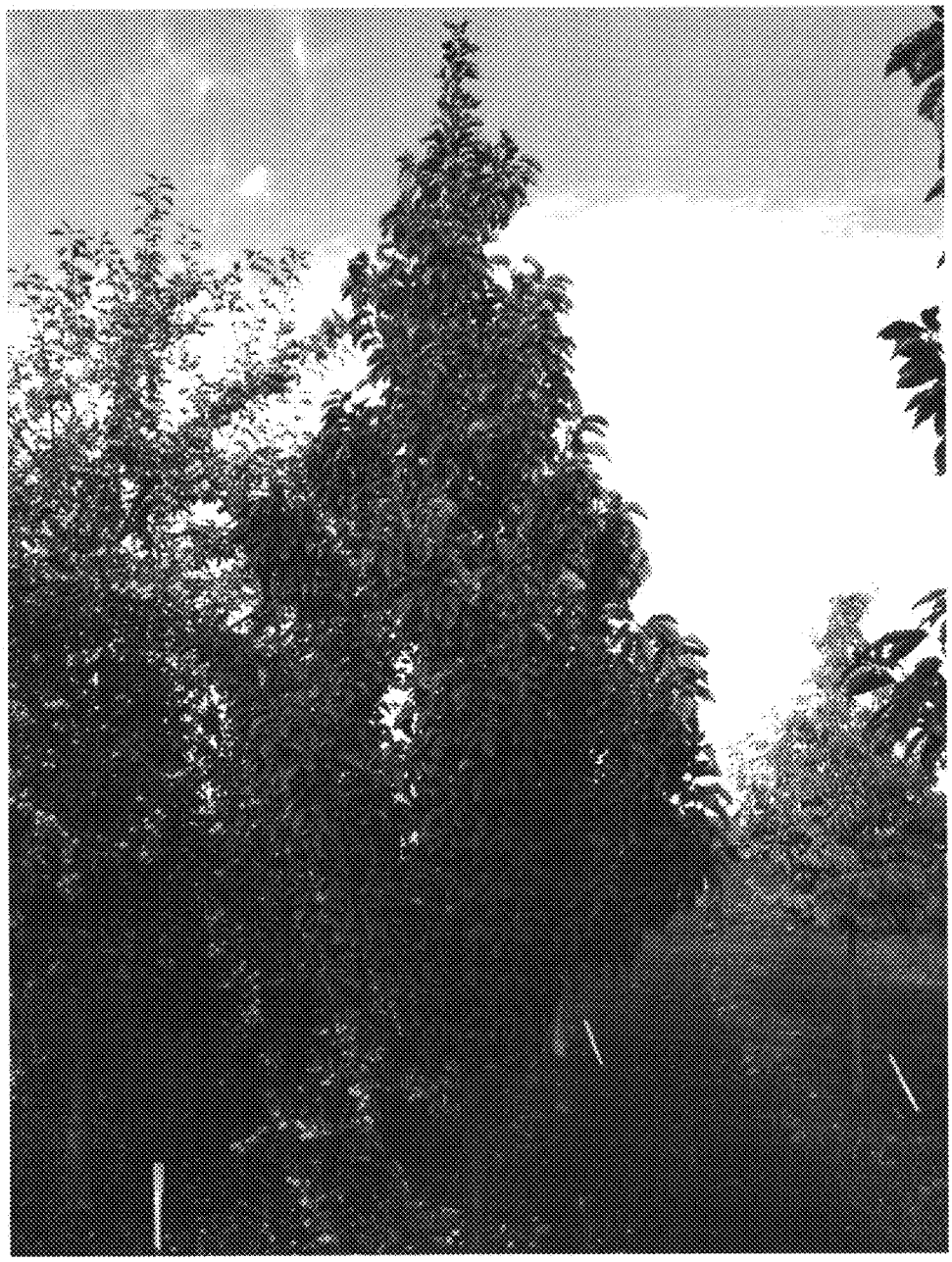
FIG. 5: Shows the original tree at 8 years of age with fruit
Figure 6:
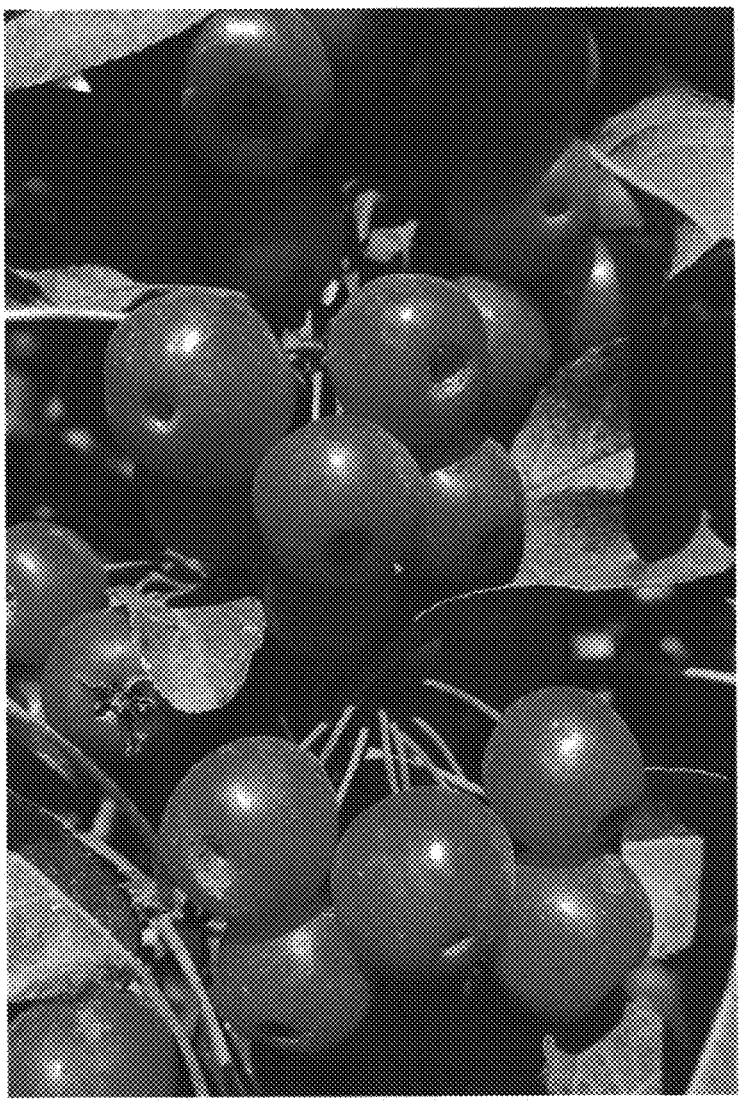
FIG. 6: Shows a close-up of the fruit on the original tree
Figure 7:
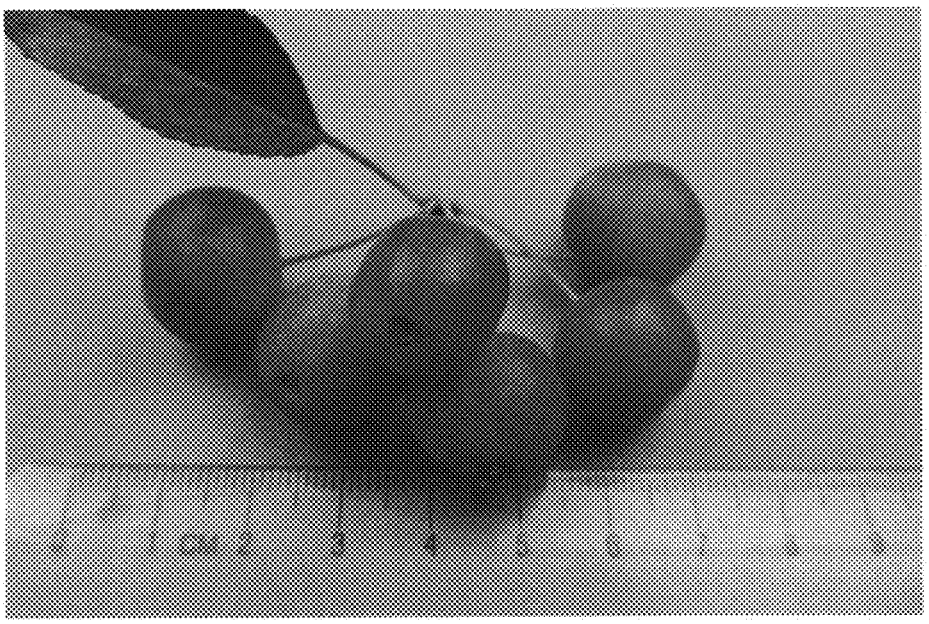
FIG. 7: Shows a close-up of fruit on a display board with a scale.
Figure 8:
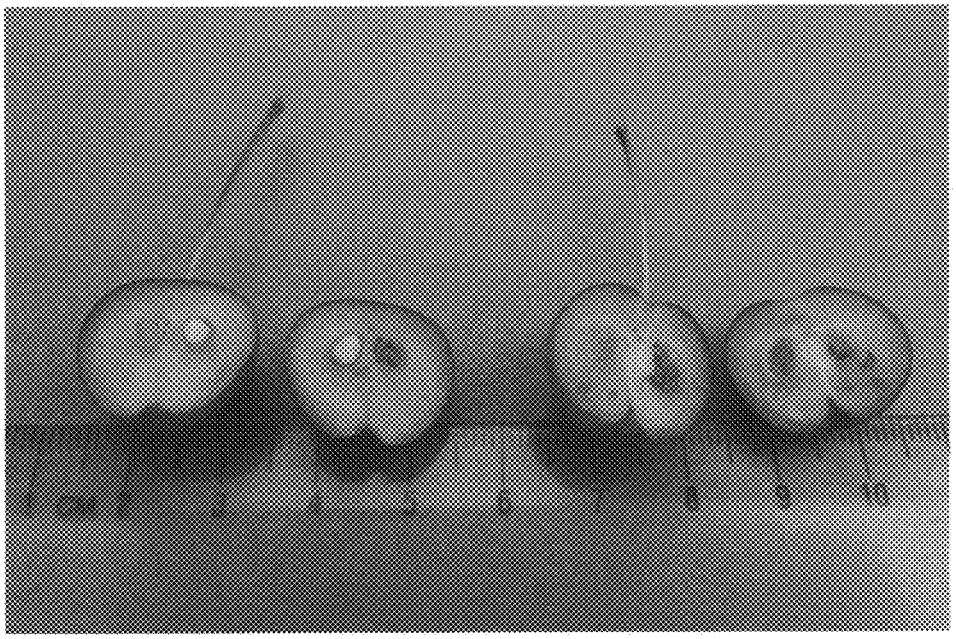
FIG. 8: Shows a close-up of fruit halved on a display board with a scale.
Figure 9:
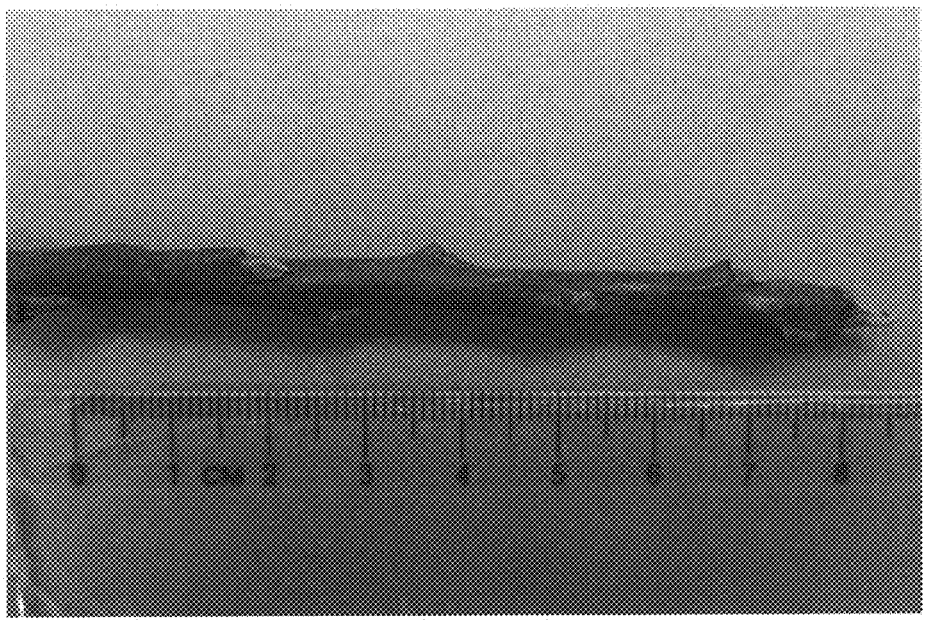
FIG. 9: Shows a dormant branch tip on a display board with a scale illustrating the short internode length.
Figure 10:
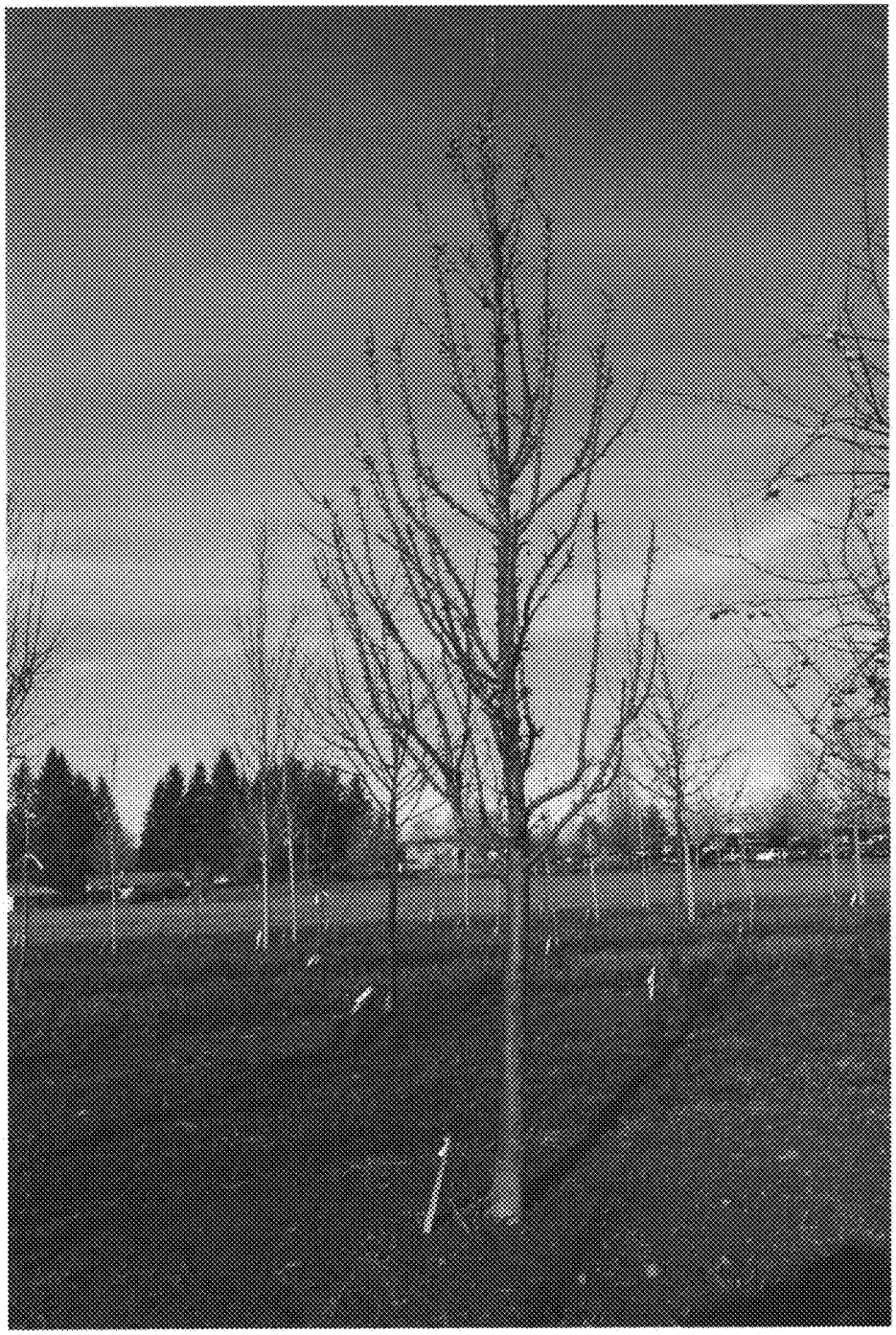
FIG. 10: Shows the original tree at 7 years of age without foliage during the winter illustrating its narrow upright columnar shape.

The following detailed description of the 'JFS KW214MX' variety is based on observations of the original tree growing in Boring, Oreg. and of two and three year old asexually reproduced progeny. The observed progeny were trees which were growing in Canby, Oreg. Color descriptions are made with reference to The Royal Horticultural Society (London) Colour Chart 1986, except where ordinary dictionary significance of color is indicated.

Scientific name: *Malus* 'JFS KW214MX'.

Parentage:

*Seed parent.*—Open pollinated seedlings of *Malus* 'KW-78MX'.

*Pollen parent.*—Unknown.

Tree:

*Overall shape.*—Narrow, upright column.

*Height.*—Original tree at 10 years of age, about 3.6 meters high.

*Width.*—Original tree at 10 years of age 1.4 meters spread.

*Caliper (trunk diameter).*—Original tree at 10 years of age, about 72 mm at 100 mm height, 58 mm at 800 mm height.

*Trunk.*—Strong and straight under nursery growing conditions.

*Trunk bark texture.*—Smooth, some vertical fissures with age.

*Trunk bark color.*—Greyed Green 197A to Greyed Green 197C.

*Immature bark color.*—Yellow Green 146A to Yellow Green 148C.

*Mature bark color.*—Greyed Orange 165A to 166B.

*Lenticels.*—Round to oval 0.5 mm×0.25 mm disappearing by the 3$^{rd}$ year. Orange White 159C in color.

*Branch color.*—Greyed Green 197B to Greyed Green 198A.

*Branch lenticels.*—Similar to those on the trunk.

*Dormant buds.*—Elongated oval with acute tip, imbricate scales, 3 mm by 5 mm.

*Internodes.*—Average internode length is about 10-16 mm on a one-year old shoot.

*Hardiness.*—Has tolerated temperatures to 10 degrees F. in Boring Oreg. which is the lowest temperature experienced in this location. It is believed to have zone 4 cold hardiness similar to other plants of the same species.

*Disease resistance.*—Excellent resistance to fireblight (*Erwinia amylovora*), powdery mildew (*Podosphaera leucotricha*) & apple scab (*Venturia inaequalis*) on foliage and fruit.

Leaves: Except as otherwise noted, observations are from twenty vigorous growth leaves.

*Arrangement.*—Alternate.

*Type.*—Simple, entire, occasionally with 1 to 2 small lobes.

*Texture.*—Smooth, slight undulation between the veins.

*Sheen.*—Slightly Glossy on upper leaf surface only.

*Length.*—Averaging 60 mm to 65 mm.

*Width.*—Averaging 40 mm to 45 mm.

*Petioles.*—20 mm to 25 mm long, about 1 mm in diameter.

*Overall shape.*—Ovate with 1 or 2 occasional side lobes.

*Margin.*—Serrulate.

*Tip.*—Acute.

*Base.*—Broadly acute.

*Stipules.*—Two per leaf, 10 mm to 15 mm long by 2 mm to 3 mm wide.

*Summer leaf color.*—Upper leaf surface: Green 131A to Green 131C. Lower leaf surface: Green 137C to Green 137D. Vein: Yellow Green 153C to Yellow Green 153D.

*Fall leaf color.*—Subdued foliage turns Yellow 6A to Yellow 7A.

*Fall color begins.*—November 5$^{st}$ (Boring, Oreg. 2017).

*Fall color peak.*—November 21$^{th}$ (Boring, Oreg. 2017).

*Fall color ends.*—November 30$^{th}$ (Boring, Oreg. 2017).

*Pubescence.*—None.

*Persistence.*—Tree is deciduous.

Flowers:

*Overall.*—Number of flowers per cluster: 5 to 6; flowers are single.

*Shape.*—Symmetrical, rounded, 5 petals, cupped.

*Size.*—Approximately 34 mm to 37 mm in diameter.

*Unopened bud.*—Red Purple 63B to Red Purple 63C.

*Petals.*—Five petals per flower, 8 mm to 10 mm wide× 16 to 20 mm long. Color White 155B. Petal shape is broadly oval to broadly obovate. Petal margins overlap.

*Sepals.*—Acute, length 2 mm×6 mm at base. Green 142A.

*Stamen.*—About 15 to 20 stamens, 8 mm to 10 mm arranged concentrically around pistil. White 155B.

*Anthers.*—Yellow Orange 18A. 1 to 1.5 mm long by 0.5 mm to 0.25 mm in diameter.

*Pistil.*—Yellow Green 145A Compound, 3 to 5 branched, length 8 mm-10 mm. Ovary inferior, typically five carpels.

*Pollen.*—Yellow 13A. Moderate amount of pollen.

*Pedicel.*—22 mm to 26 mm long by 0.5 mm to 0.6 mm in diameter. Yellow Green 146B to Yellow Green 146C.

*Pubescence.*—Yes on the upper side of the sepal.

*Fragrance.*—Slightly sweet.

*Flowering date.*—In Boring, Oreg. 2017. First bloom April 23th, peak bloom May 1st, last bloom May 15th. (Bloom was about 2 weeks later than average at this location in 2017 due to cold spring weather).

Fruit: Observations are from a sampling of typical fruit.

*Cluster.*—4 to 8 fruits per cluster.

*Size.*—Typical fruit is 14 mm to 18 mm in diameter by 13 mm to 15 mm long.

*Shape.*—Rounded, flattened, slightly wider than long.

*Skin.*—Smooth.

*Lenticels.*—None observed.

*Calyx.*—Sometimes present at maturity.

*Color.*—Immature summer fruit is Yellow Green 144C ripening to Red 45A in October; then finally Red 34A when fully ripe in October.

*Seeds.*—Typically 3 per fruit, ovoid to rounded, about 4 mm long and about 3 mm wide with a smooth surface, Greyed Orange 164A to Greyed Orange 164C in color.

*Fruit production.*—Moderate to heavy depending on the year.

*Fruit persistence.*—90% still persistent Nov. 15 (2017).

*Usage.*—Ornamental, non-edible.

COMPARISON TO THE SEED PARENT

Compared to the seed parent tree 'KW-78MX', my new cultivar, 'JFS KW214MX', has fruit which is 14-18 mm in diameter, ripens to Red 45A to Red 34A and persists with good ornamental quality in November while 'KW-78MX has 20-25 mm diameter fruit that ripens to yellow and begins softening and turning brown in October. In addition, 'JFS KW214MX' is highly resistant to apple scab disease whereas 'KW-78MX' is only moderately resistant to this disease.

COMPARISON TO OTHER SIMILAR VARIETY

| | Malus 'JFS W214MX' | Malus 'Durleo' PP20167 | Malus 'JFS KW213MX' |
|---|---|---|---|
| Form | Narrow upright column | Compact upright oval. | Narrow upright column |
| Leaf Length | 60 mm to 65 mm | 85 mm | 80 mm to 90 mm |
| Leaf Width | 40 mm to 45 mm | 43 mm | 40 mm to 50 mm |
| Petiole | 20-25 mm | 27 mm | 20 mm |
| Spring Upper Leaf Color | Green 131A to 131C | Green 143B | Red Purple 59A to Purple 79B |
| Branch Color | Greyed Green 197A to Greyed Green 197C | Greyed Purple 183B | Purple 79A to 79C |
| Bark on trunk | Smooth, some vertical fissures. | Bole like bumps | Smooth with vertical fissures |
| Branch Angles on 2 YR trees | 40-50 degrees | 60-70 degrees | 40-50 degrees |
| Fruit Color | Red 45A to Red 34A | Red Purple 59A | Red 44A to Red 46A |
| Fruit Size | 13 to 14 mm long × 14-18 mm wide | 10 mm × 10 mm | 15 to 17 mm × 16-18 mm |
| Fruit Shape | Round to slightly flattened | Round | Round to slightly oval |

COMPARISON OF AVERAGE INTERNODE LENGTH

When compared to other commercial ornamental crab apple varieties 'JFS KW214' has significantly shorter average internode lengths.

| Cultivar | Average internode length |
|---|---|
| Malus 'JFS KW214MX' | 10-16 mm |
| Malus 'JFS-KW5' (PP14,375) | 25-30 mm |
| Malus 'Perfect Purple' (unpatented) | 25-30 mm |
| Malus 'Spring Snow' (unpatented) | 30-35 mm |
| Malus 'Prairiefire' (unpatented) | 30-35 mm |
| Malus 'Profusion' (unpatented) | 25-30 mm |

I claim:

1. A new and distinct variety of crabapple tree, as herein illustrated and described.

* * * * *